United States Patent
Jain et al.

(10) Patent No.: US 11,547,487 B2
(45) Date of Patent: Jan. 10, 2023

(54) SCANNER INDEPENDENT ULTRASONIC TRACKING OF INTERVENTIONAL INSTRUMENTS HAVING AN ACOUSTIC SENSOR BY MEANS OF HAVING AN ADDITIONAL ACOUSTIC TRANSDUCER COUPLED TO ULTRASOUND IMAGING PROBE

(71) Applicant: KONINKLIJKE PHILIPS N.V., Eindhoven (NL)

(72) Inventors: Ameet Kumar Jain, New York, NY (US); Francois Guy Gerard Marie Vignon, Hudson, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1634 days.

(21) Appl. No.: 14/898,783

(22) PCT Filed: Jun. 25, 2014

(86) PCT No.: PCT/IB2014/062579
§ 371 (c)(1),
(2) Date: Dec. 16, 2015

(87) PCT Pub. No.: WO2014/207666
PCT Pub. Date: Dec. 31, 2014

(65) Prior Publication Data
US 2016/0367322 A1 Dec. 22, 2016

Related U.S. Application Data

(60) Provisional application No. 61/840,500, filed on Jun. 28, 2013.

(51) Int. Cl.
*A61B 34/20* (2016.01)
*A61B 8/00* (2006.01)
(Continued)

(52) U.S. Cl.
CPC .............. *A61B 34/20* (2016.02); *A61B 5/06* (2013.01); *A61B 5/6847* (2013.01);
(Continued)

(58) Field of Classification Search
CPC .......... A61B 34/20; A61B 8/481; A61B 8/54; A61B 8/0841; A61B 5/6847; A61B 5/06;
(Continued)

(56) References Cited

U.S. PATENT DOCUMENTS

| 4,249,539 A | 2/1981 | Vilkomerson et al. |
| 4,407,294 A | 10/1983 | Vilkomerson |

(Continued)

FOREIGN PATENT DOCUMENTS

| JP | 4129543 A | 4/1992 |
| WO | 9216148 A1 | 10/1992 |

(Continued)

OTHER PUBLICATIONS

Mung et al Design and in vitro evaluation of a real-time catheter localization system using time of flight measurements from seven 3.5 MHz single element ultrasound transducers towards abdominal aortic aneurysm procedures (Ultrasonics vol. 51, Issue 6, Aug. 2011, pp. 768-775) (Year: 2011).*

(Continued)

*Primary Examiner* — Serkan Akar (57) ABSTRACT

A system for tracking an instrument with ultrasound includes a probe (122) for transmitting and receiving ultrasonic energy and a transducer (130) associated with the probe and configured to move with the probe during use. A medical instrument (102) includes a sensor (120) configured to respond to the ultrasonic energy received from the probe. A control module (124) is stored in memory and configured to interpret the ultrasonic energy received from the probe and the sensor to determine a three dimensional location of (Continued)

the medical instrument and to inject a signal to the probe from the transducer to highlight a position of the sensor in an image.

9 Claims, 10 Drawing Sheets (51) Int. Cl.
| | |
|---|---|
| *A61B 8/08* | (2006.01) |
| *A61B 5/00* | (2006.01) |
| *A61B 5/06* | (2006.01) |
| *A61B 90/00* | (2016.01) |
| *A61B 17/34* | (2006.01) |
| *G01S 7/52* | (2006.01) |
| *G01S 15/89* | (2006.01) |
| *G01S 15/74* | (2006.01) |

(52) U.S. Cl.
CPC ............ *A61B 8/0841* (2013.01); *A61B 8/481* (2013.01); *A61B 8/54* (2013.01); *G01S 7/52073* (2013.01); *G01S 15/74* (2013.01); *G01S 15/899* (2013.01); *A61B 2017/3413* (2013.01); *A61B 2034/2063* (2016.02); *A61B 2090/3784* (2016.02)

(58) Field of Classification Search
CPC .... A61B 2090/3784; A61B 2034/2063; A61B 2017/3413; G01S 7/52073; G01S 15/899; G01S 15/74
See application file for complete search history.

(56) References Cited

U.S. PATENT DOCUMENTS

| | | | |
|---|---|---|---|
| 5,158,088 A | | 10/1992 | Nelson et al. |
| 5,161,536 A | | 11/1992 | Vilkomerson et al. |
| 5,513,640 A | * | 5/1996 | Yamazaki ............ G01N 29/0609 600/451 |
| 5,779,638 A | | 7/1998 | Vesely et al. |
| 5,797,849 A | * | 8/1998 | Vesely .................... G01S 15/88 600/461 |
| 5,921,930 A | | 7/1999 | Uberle |
| 6,592,526 B1 | | 7/2003 | Lenker |
| 8,200,313 B1 | | 6/2012 | Rambod et al. |
| 2003/0060700 A1 | | 3/2003 | Solf et al. |
| 2004/0002658 A1 | | 1/2004 | Marian, Jr. |
| 2007/0149880 A1 | * | 6/2007 | Willis ................... A61B 8/0841 600/471 |
| 2011/0245659 A1 | * | 10/2011 | Ma ......................... A61B 5/066 600/424 |
| 2013/0041252 A1 | | 2/2013 | Vignon et al. |
| 2013/0046230 A1 | * | 2/2013 | Lewis, Jr. ......... A61M 37/0092 604/22 |
| 2013/0116538 A1 | | 5/2013 | Herzog et al. |
| 2013/0245433 A1 | * | 9/2013 | Deladi ................. A61B 8/0883 600/424 |
| 2016/0038119 A1 | * | 2/2016 | Desjardins ........... A61B 8/4494 600/424 |
| 2016/0270760 A1 | * | 9/2016 | Janicki ................... A61B 8/463 |

FOREIGN PATENT DOCUMENTS

| | | |
|---|---|---|
| WO | 2005055849 A1 | 6/2005 |
| WO | 2011138698 A1 | 11/2011 |
| WO | 2012024201 A1 | 2/2012 |
| WO | 2012066437 A1 | 5/2012 |
| WO | 2013001437 A1 | 1/2013 |
| WO | 2014207728 A1 | 12/2014 |

OTHER PUBLICATIONS

20160038119 Desjardins Foreign Priority GB1307551 (Year: 2013).*
Breyer B., et al., "Ultrasonically Marked Catheter—A Method for Positive Echographic Catheter Position Identification", Medical and Biological Engineering and Computing, Springer, Heildelberg, DE, vol. 22, No. 3, May 1, 1984, pp. 268-271.
Merdes, et al., "Locating a Catheter Transducer in a Three-Dimensional Ultrasound Imaging Field", IEEE Transactions on Biomedical Engineering, vol. 48, No. 12, Dec. 2001, pp. 1444-1452.
Nikolov, et al., "Precision of Needle Tip Localization Using a Receiver in the Needle", 2008 IEEE International Ultrasonics Symposium Proceedings, Digital Object Identifier: 10.1109/ULTSYM.2008.0117, pp. 479-482.
Mung, et al., "A non-disruptive technology for robust 3D tool tracking for ultrasound-guided interventions." Medical Image Computing and Computer-Assisted Intervention—MICCAI 2011. Springer Berlin Heidelberg, 2011. pp. 153-160.

* cited by examiner

SCANNER INDEPENDENT ULTRASONIC TRACKING OF INTERVENTIONAL INSTRUMENTS HAVING AN ACOUSTIC SENSOR BY MEANS OF HAVING AN ADDITIONAL ACOUSTIC TRANSDUCER COUPLED TO ULTRASOUND IMAGING PROBE

CROSS-REFERENCE TO PRIOR APPLICATIONS

This application is the U.S. National Phase application under 35 U.S.C. § 371 of International Application No. PCTB2014/062579, filed on Jun. 25, 2014, which claims the benefit of U.S. Provisional Patent Application No. 61/840,500, filed on Jun. 28, 2013. These applications are hereby incorporated by reference herein.

BACKGROUND

Technical Field

This disclosure relates to medical instruments and more particularly to scanner independent ultrasonic tracking of medical devices.

Description of the Related Art

Needles, catheters and other interventional tools are often difficult to visualize under ultrasound due to their specular nature and unfavorable incidence angles. One solution for marking a needle tip under ultrasound guidance is to embed a small ultrasound sensor at the tip of the needle. Such a sensor receives the direct ultrasound signals that impinge upon it as imaging beams from an ultrasound imaging probe sweep of the field of view. Different ways of using these signals to highlight the position of the transducer in the ultrasound image have been proposed. These ways rely on time-of-flight of ultrasound from the imaging probe to the sensor for estimating the range coordinate of the sensor, and on the intensity of the received signals as the imaging beams sweep the field of view to recover the lateral coordinate. To estimate time of flight, one must have access to the line trigger events of the scanner, and to estimate the lateral coordinates, one must have access to the frame trigger event and to the coordinates and steering angles of the imaging beams.

SUMMARY

In accordance with the present principles, a system for tracking an instrument with ultrasound includes a probe for transmitting and receiving ultrasonic energy, a transducer associated with the probe and configured to move with the probe during use and a medical instrument including a sensor configured to respond to the ultrasonic energy received from the probe. A control module is stored in memory and is configured to interpret the ultrasonic energy received from the probe and the sensor to determine a three dimensional location of the medical instrument and to inject a signal to the probe from the transducer to highlight a position of the sensor in an image.

A method for determining a position of an instrument includes estimating a frame rate of an imaging probe; analyzing traces within a detection window to find a temporal maximum which best matches a position of a sensor mounted on an instrument to determine an arrival time; injecting an acoustic feedback signal into the imaging probe using a transducer on the imaging probe to simulate an echo back from the sensor mounted on the instrument; and displaying the echo in an image to identify the position of the instrument.

A method for determining a position of an instrument includes estimating a frame rate of an imaging probe; dividing up an image into individual beams to establish a location of an individual beam in the image; analyzing traces to find a temporal maximum which best matches a position of a sensor mounted on an instrument to determine an arrival time; computing at least one of: a location of the sensor using a transmission time from the probe and a receive time at the sensor, and a beam number on which the location of the sensor lies to determine the position of the sensor; and overlaying an indicator on the image to visually indicate the location of the instrument.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with the present principles, system and methods permit highlighting of a position of a sensor with less reliance on a scanner. A frame, line triggers and beamforming parameters are no longer needed. This allows ultrasound-equipped tools to be self-contained (no need for low-level interfacing with the scanner) thus allowing them to be usable with a broad installed base of ultrasound machines from any vendor. In one embodiment, the system is capable of on-the-fly reverse-engineering of crucial parameters from the imaging scanner, e.g., frame rate and line trigger positions, analog acoustic signal injection into the scanner's receive signal path, etc.

A smart device in accordance with the present principles can detect when ultrasound (US) beams are fired; and additionally inject a signal right at a probe-head. This smart device can be semi-permanently or permanently attached to the probe. Alternately, since most interventions use a glove to maintain sterility, a piezoelectric material such as, e.g., polyvinylidene fluoride (PVDF) or poly(vinylidene fluoride-co-trifluoroethylene) (P(VDF-TrFE)) can be integrated into a disposable glove. Since PVDF strips can be manufactured at ultra-low costs, both these options are attractive. Additionally, the glove could be composed of a single strip or could utilize multiple strips to achieve a higher resolution.

In addition to the PVDF strip, a passive acoustic sensor or sensors are provided on the needle or instrument. The sensor could be made of lead zirconium titanate (PZT) or piezoelectric polymer or any other piezoelectric material. As the unknown US probe fires its beams, a control box (or computer) will receive the signals from both the sensor on the device and from the PVDF strip on the probe. Together, an algorithm will compute the time when the individual beams were sent out, the time when the signal was received at the needle or instrument, and hence the 3D location of the needle or instrument. To mark the location of the needle in the image, the control box will 'inject' a small signal in the US probe using the PVDF strip on the probe. This injected acoustic signal will be perceived by a scanner as a response to its own acoustic field. This signal will be processed by the scanner's beamforming pipeline and ultimately, visualized on the US image (highlighting the needle or device location). A multi-strip embodiment will permit fine-tuning of the quality of the injected signal by injecting different signals into different beams and with different phases.

It should be understood that the present invention will be described in terms of needles; however, the teachings of the present invention are much broader and are applicable to any medical instruments or other instruments tracked by acoustic energy. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the Figures may be implemented in various combinations of hardware and software and provide functions which may be combined in a single element or multiple elements. The present embodiments may be employed any time an instrument is inserted into the body under ultrasound guidance, this includes needle procedures (biopsies, ablation, anesthesia, pain management, abscess drainage, etc.) and catheter procedures (heart repair, electrophysiology, etc.).

The functions of the various elements shown in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1:
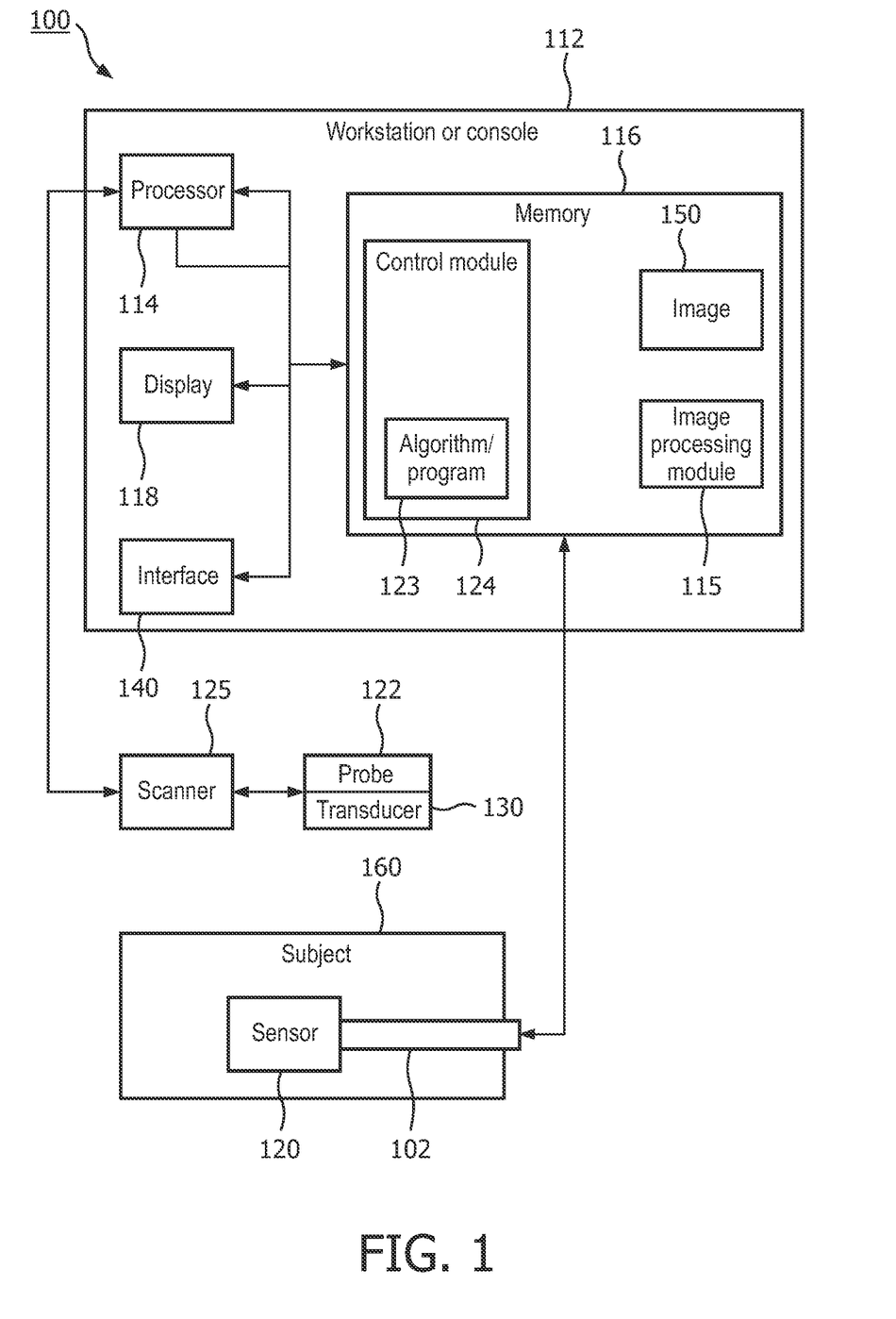
FIG. 1 is a block/flow diagram showing a system for tracking an instrument with ultrasound in accordance with one embodiment.

Referring now to the drawings in which like numerals represent the same or similar elements and initially to FIG. 1, a system 100 is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store an image processing module 115 configured to process signals from an ultrasonic scanner 125. Module 115 is configured to use the US signals to reconstruct structures deformations, deflections and other changes associated with a medical device, instrument or tool 102 and/or its surrounding region. The medical device 102 may include a needle, a catheter, a guidewire, a probe, an endoscope, a robot, an electrode, a filter device, a balloon device, or other medical component, etc.

An acoustic sensor (or receiver, transducer) 120 is mounted on the medical device 102 to be highlighted, and a second transducer (or sensor) 130 is mounted on a probe 122, such as an US probe 122. For ease of reference, the sensor on the probe 122 will be referred to as a transducer 130 and the sensor on the device 102 will be referred to as sensor 120. The probe 122 is connected to the US scanner 125, which transmits and receives US energy provided in a patient or subject 160. The surface of probe 122 is capable of reception (to sense signal emission by the probe 122, thus effectively reverse-engineering the line trigger information) and capable of transmission, thus effecting acoustic signal injection directly at the probe 122 into a beamforming signal path. The received signals at the probe 122 are coupled to a simple data-analysis and control module 124 stored in memory 116 and capable of some amount of signal processing in algorithm/program 123 (e.g., Fast Fourier Transform (FFT), max identification, optional curve fitting, etc.).

In one embodiment, the ultrasound sensor 120 is placed at a tip of the medical instrument 102, e.g., a needle. The sensor 120 senses ultrasound signals as beams from a sweep of the field of view of the imaging probe 122. These ultrasound signals are analyzed to extract a frame repetition period T, and a time of arrival $t_0$ of the maximum signal at the sensor 120. At the same time, the ultrasound transducer 130 (at the probe surface) senses the beams being emitted by the probe 122, which is effectively equivalent to line trigger information. A differential time $t_d$ between the arrival times of the strongest beam (to) and the time that beam was emitted is the ultrasound time of flight from the probe 122 to the tracked sensor 120. One or two frames later, the transducer 130 at the probe surface is turned on and emits a pulse at $t_0+T+t_d$ (or $t_0+2T+t_d$) directly into the probe 122. A scanner 125, connected to the probe 122, interprets this pulse as being a high echo coming from the position of the sensor 120, thus highlighting it on an image 150 even under slight out-of-plane alignment.

When the device 102 is inserted inside a US region, a one-time calibration step may be run to estimate a frame rate (T) of the imaging mode being used. The timing of the line trigger events is captured by analyzing the signal received by the transducer 130 (e.g., PVDF material) at the probe surface. A temporal maximum ($t_0$) of the signals received by the sensor 120 is found, and the differential time $t_d$ between $t_0$ and the immediately preceding line trigger corresponds to the sound travel time from the probe 122 to the sensor 120 on the device 102. Injecting signal on the following frames (at $t_0+nT+t_d$, n being an integer) creates an acoustic signal that seems to come from the sensor position on the device 102, at subsequent frames (an additional delay of $t_d$ needs to be inserted to simulate ultrasound propagation back from the device 102 to the probe 122).

It should be understood that two methods have been described for synchronizing frame rate. These include, as described, 1) placing an asymmetric strip (piezoelectric) on the imaging probe 122. In this way, even the start of frame lines can be identified, and 2) listening to the signal received on the sensor 120 on the tool 102 for a relatively long period of time, and estimating frame rate by Fourier analysis. The second method needs the instrument to already be inside the body for frame rate estimation, and even though the frame rate is known, the beam that starts the frame is not known.

A display 118 shows an echo coming from the sensor location. Display 118 may also permit a user to interact with the workstation 112 and its components and functions, or any other element within the system 100. This is further facilitated by an interface 140 which may include a keyboard, mouse, a joystick, a haptic device, or any other peripheral or control to permit user feedback from and interaction with the workstation 112.

In another embodiment, a video signal-out from the scanner 125, the instrument 102 with the sensor 120 (e.g., a PVDF strip or strips) and the transducer 130 attached to the US probe 122 are employed to compute a 3D location of the instrument 102 at any given time. The video-out signal is easily available on commercial scanners and is streamed into the computational workstation 112. An appropriate image is cropped and segmented to identify left-right beams/bounds. At any given moment, the PVDF strip or transducer 130 on the US probe 122 provides a signal (A) when any of the US beams have been fired. This signal goes to the control module 124. Additionally, the instrument 102 having the acoustic sensor(s) 120 also receives this acoustic wave and converts it into an electrical signal (B), which also goes to the control module 124. The control module 124 is itself included in the computational workstation 112. When the system starts, only the A-signals are measured, and used to identify the inter-beam time and the inter-frame time.

Figure 10:
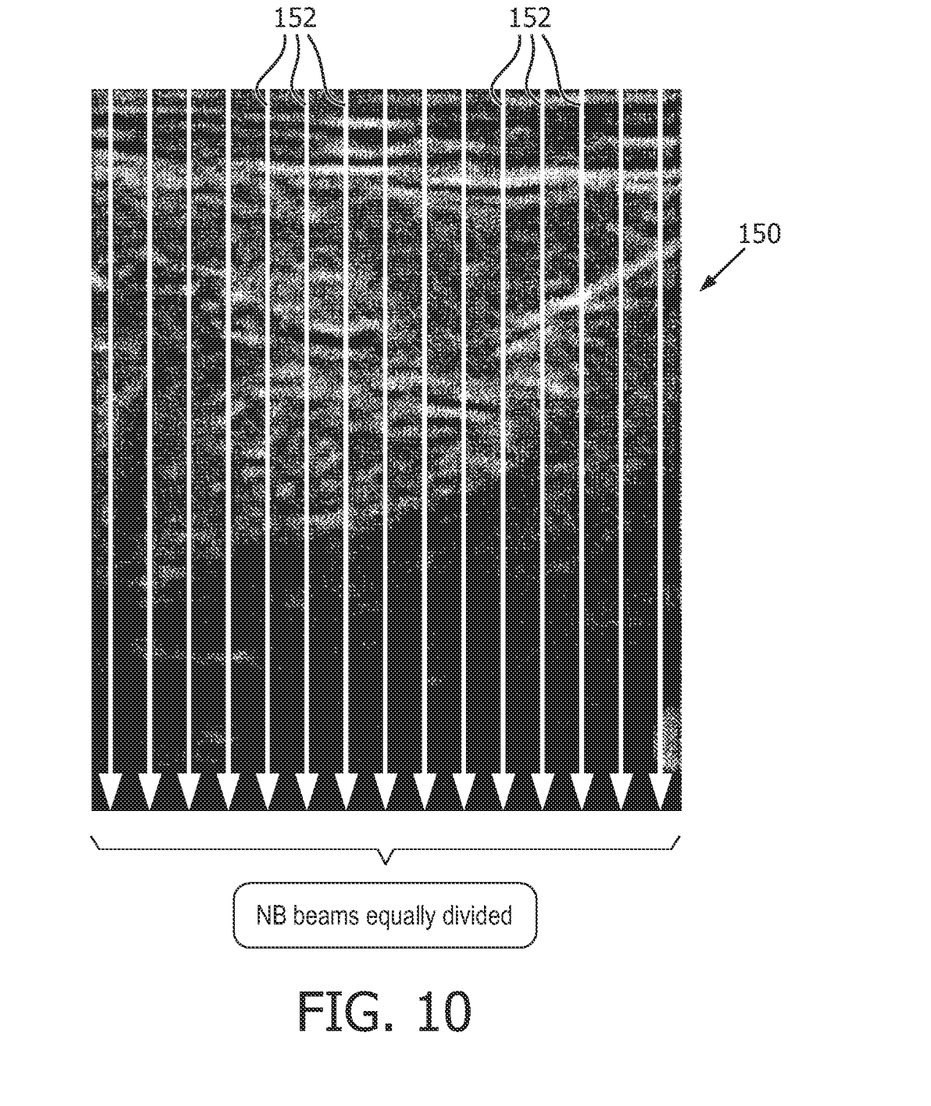
FIG. 10 is an image divided up by lines corresponding to ultrasonic beams in accordance with the present principles.

After the initial calibration step, the number of beams (NB), inter-beam times, and frame-rate are known. The real-time video-out image of the US probe 122 is now used to segment out the US field of view, which is then divided to identify the position of each beam in the image. For most scanners/images, equally dividing an image 150 into NB scan-lines 152 will suffice as depicted in FIG. 10. When the instrument 102 is inserted, the instrument 102 receives a signal based on its location inside the image. A primary beam that contains the sensor 120 can be automatically detected based on the maximum interpolated signals. Post-calibration, the range/depth of the sensor 120 can also be computed from the time difference between the emission of the beam (signal-A) and the beam hitting the sensor 120 (signal-B). Note that this information is now available since signal-A and signal-B are time-synced as they are connected to the same control module 124. Additionally, since the beam position in the video image has already been established, the instrument (sensor 120) position can now be displayed on top of the US image in real-time.

The beam-parameters can be recalibrated every time a change is detected in the video-out image. Additionally, the instrument 102 may have more than one sensor implanted, and the signals from the sensors could be used to estimate its out-of-plane position. The instrument 102 preferably utilizes PZT or PVDF or P(VDF-TrFE), though polymers are more convenient to use. Variations of this embodiment could include different visualizations (e.g., the image of the echo may be shaped to any desirable or convenient shape), or multiple mounting embodiments. Furthermore, to make the method easier to implement, the PVDF strip could be made to consist of two strips—one on the left and the other on the right. This would break the symmetry in the beam-firing patterns and help differentiate the start of the image-frame (first beam on one strip) from the end (last beam on the other strip), thereby measuring the frame rate without the need to analyze signals from the sensor 120. Alternately, the strip could be cut in a non-symmetric manner to generate a non-symmetric profile as the fired beams move left to right. The strip could both be made to be disposable or permanent.

Figure 2:
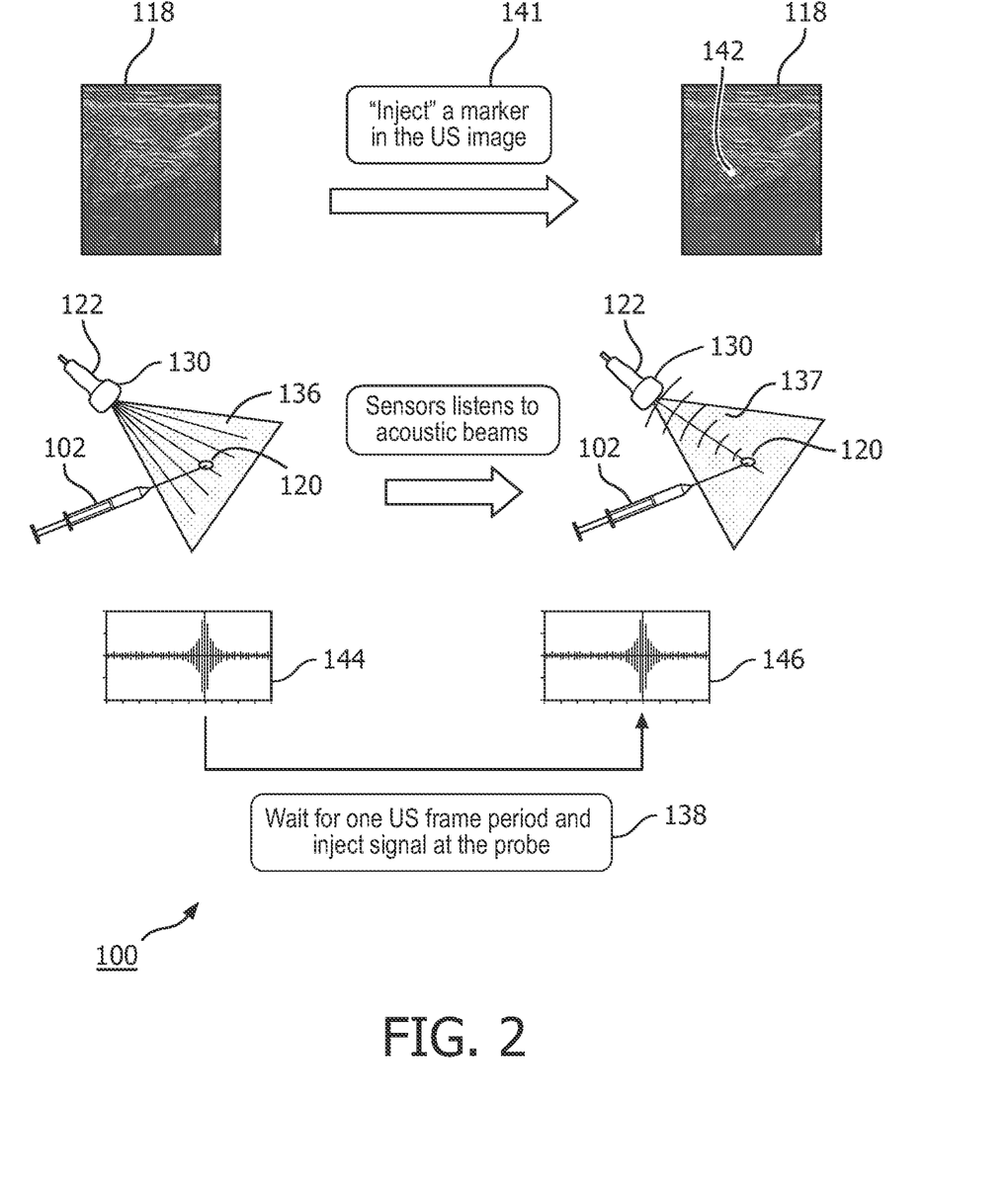
FIG. 2 is a conceptual diagram showing a system for tracking the instrument with ultrasound in accordance with one embodiment.

Referring to FIG. 2, a conceptual diagram shows interaction between components in accordance with one illustrative embodiment. Signal injection is performed with the transducer 130 at the surface of probe 122. The sensor 120 is placed at the tip of the device 102 to be highlighted. Example signals 136, 137 received by that sensor 120 during one imaging frame and then by a delay beam from the probe 122 are shown. The system 100 identifies the position of the maximum and its timing relative to the line trigger information in plots 144 and 146 (after delay) gathered by the sensor 130 at the probe 122. One frame period 138 later, a signal 141 is injected by the transducer 130 at the probe 122 with the appropriate timing to generate a bright echo 142 that seems to come from where the sensor 120 is located and is visible on the display 118.

Figure 3:
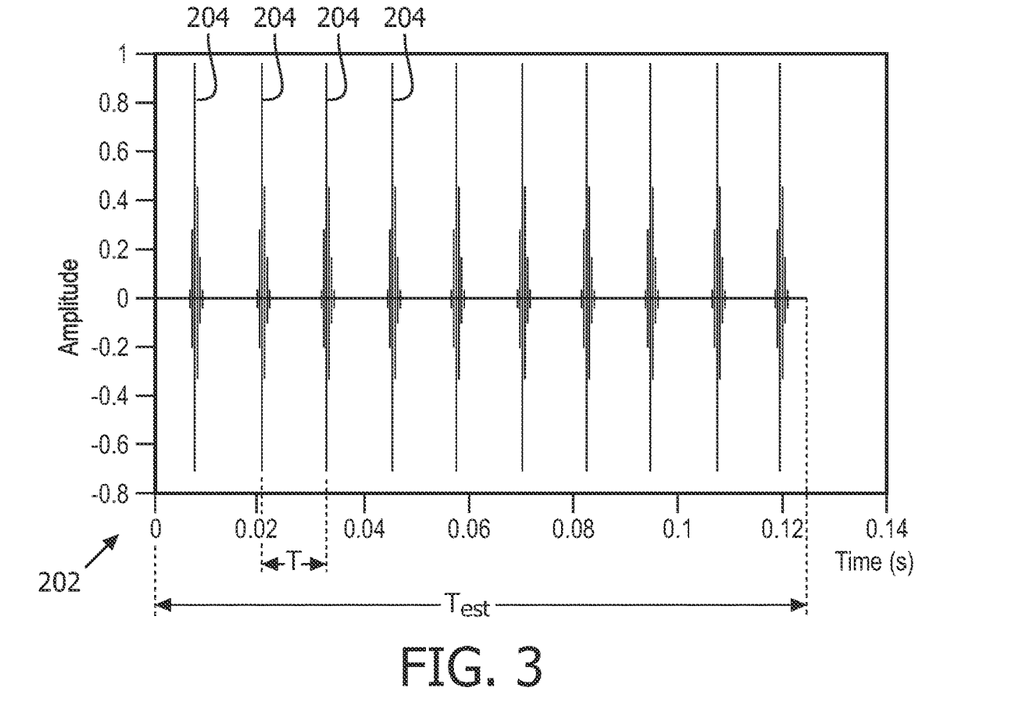
FIG. 3 is a plot of amplitude versus time showing ultrasound pulses for estimating frame rate in accordance with one embodiment.

Referring to FIG. 3, a frame rate T of the imaging probe needs to be estimated. In one embodiment, this is done by listening to a received signal for a relatively long time $T_{est}$ (e.g., a quarter of a second, to record, e.g., 10 frames at 40 Hz) and analyzing the signal for its dominant period, i.e., by Fourier analysis. A received trace 202 is depicted in FIG. 3. On the trace 202, individual impulses 204 correspond to different beams hitting the sensor (120 on the device 102) (the amplitude varies as beams get closer and then farther from the sensor 120). The pattern is then repeated several times as several identical frames are acquired in continuous sequence. The trace 202 received by the sensor (120) during a time $T_{est}$ can be used to estimate the frame rate T of the system. Once this is done, the receiver system analyzes traces of a length $T_{detect}$ ($T<T_{detect}<2T$ ideally). Alternatively, the frame rate can be estimated by placing a non-symmetric arrangement of transducers 130 on the probe 122. Signals collected by transducer 130 as the probe 122 emits beams that span the field of view will exhibit a periodicity that corresponds to the frame rate, and the timing of start-of-frames can be estimated.

Figure 4:
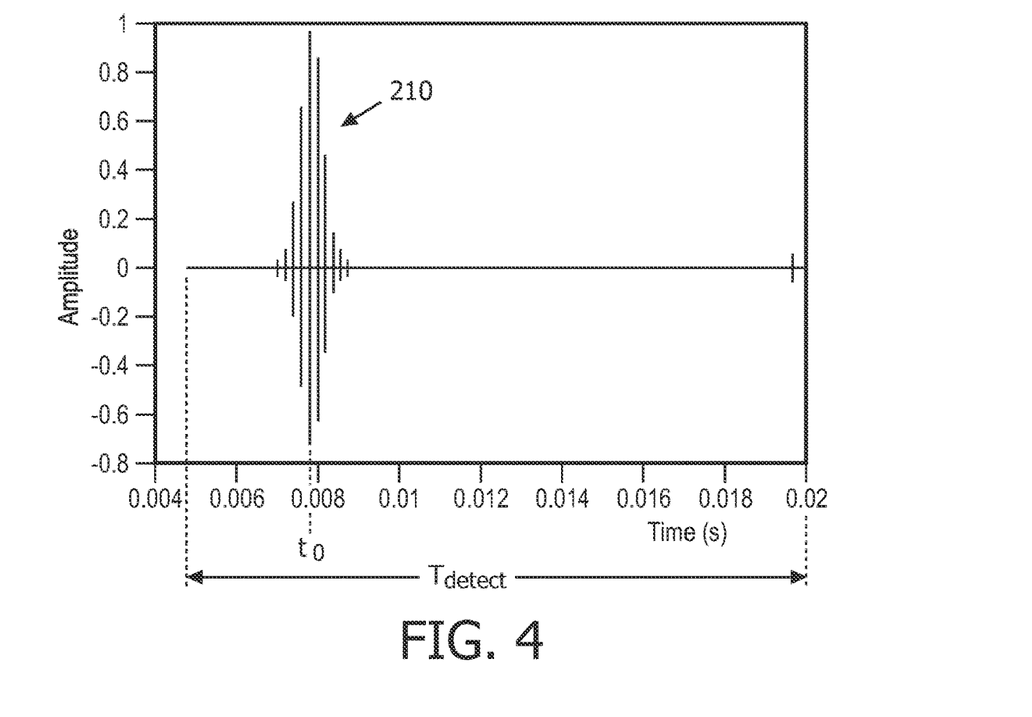
FIG. 4 is a plot of amplitude versus time showing an ultrasound pulse for determining a detection time in accordance with one embodiment.

Referring to FIG. 4, one of the pulses 204 is shown as trace 210 with a length $T_{detect}$ depicted. Note that acquisition of these traces 210 is not necessarily synchronized with the frame rate. The system searches for the temporal maximum $t_0$ of this trace. That maximum corresponds to the instant when the pulse from the transmit event that is best aligned with the sensor 120 reaches the sensor 120. The trace received by the sensor 120 during a time $T_{detect}$ (e.g., $T_{detect}=1.2T$ here) is used to find the time to when the most on-axis transmit reaches the sensor 120. $t_0$ is simply the temporal maximum of the trace.

Instead of a simple peak detection for identifying the beam closest to the sensor 120 and the arrival time, it may be advantageous to fit the curve or trace 210 (e.g., signals received by the sensor 120 during $T_{est}$) and fit the curve 210 to the local maxima of the individual pulses to a simple signal model, e.g., a Gaussian.

Next, an acoustic signal is injected back into the imaging probe 122 to create an artificial echo that seems to come from the sensor position. It may also be desirable for the injected acoustic signal to blink (short periods of "injection on" alternating with periods of "injection off"). The human eye is more sensitive to a blinking signal. If the videostream is captured and synchronized to the signal acquisition and injection setup, differential images can be generated to highlight the injected signal (the "blink off" image is subtracted from the "blink on" image). The differential images can be enhanced and superimposed on the original image in an entirely image-processing chain that only requires access to video data from the scanner. The shapes of the marker in the display image may take on any shape and other visual effects may be employed as well.

Two embodiments are envisioned: the transducer at the probe is a transponder (can be switched into a transmit mode with a slow T/R switch), or two transducers, one sensing, and one emitting, are placed at the probe surface. Either way, the sequence of events depicted in FIG. 5 applies.

Figure 5:
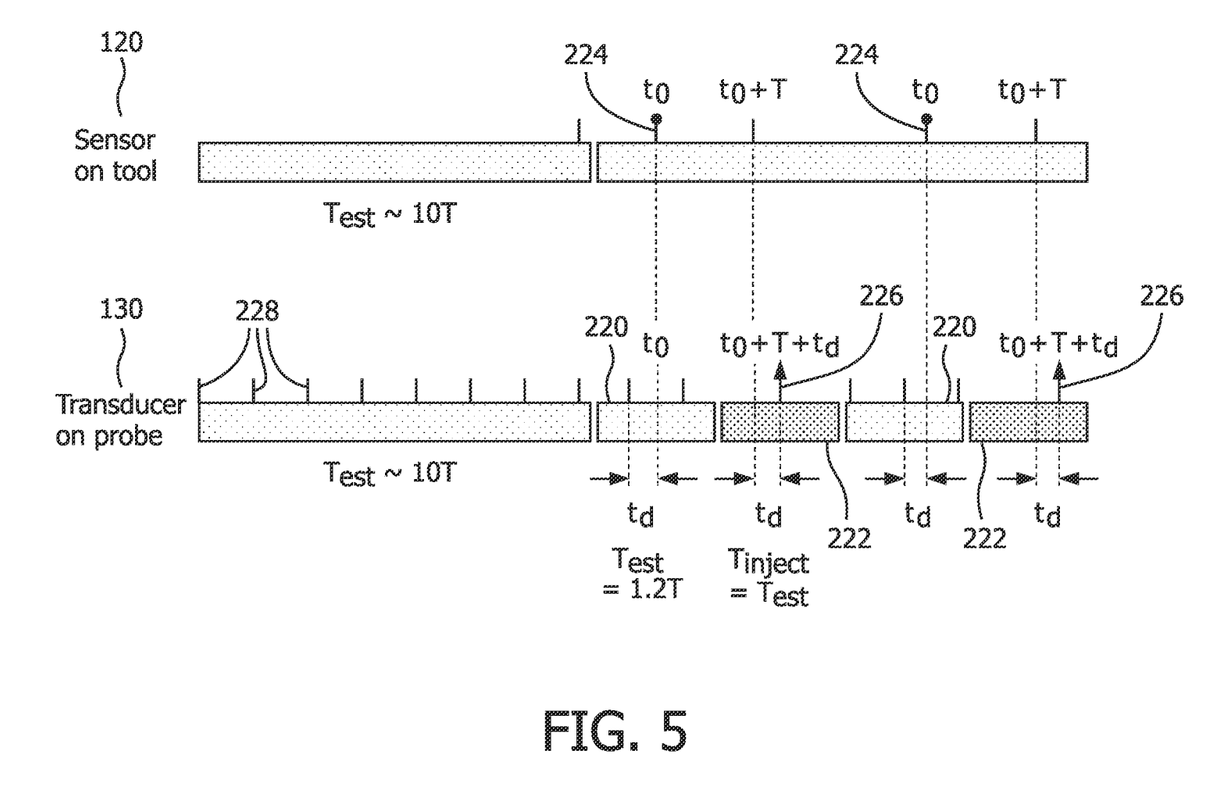
FIG. 5 is an event time line showing events occurring between a transducer on a probe and a sensor of an instrument or tool in accordance with one embodiment.

Referring to FIG. 5, a sequence of events for frame rate estimation, peak pulse detection, and pulse injection is illustratively shown. Events at the sensor 120 on the tool 102 are shown in an upper region and events at the transducer 130 on the probe 122 are shown in a lower region. A relatively long $T_{est}$ (long enough to comfortably span tens of frames) is employed to estimate the imaging system's frame rate. Then, peak detection at the tool/line trigger detection at probe periods 220 alternate with signal injection periods 222 at the probe. If a signal peak is detected at a time $t_0$ on the tool, a signal is injected at $t_0+T+t_d$, this creates an artificial echo at the position of the transponder one frame after its detection. Detection events 224 are depicted as rounded ends, injection events 226 are arrows, and line triggers 228 are straight segments.

After detection of the signal's arrival time to, an impulse is sent from the transponder or transmitter at a time $t_0+nT+t_d$, n being an integer, preferably n=1, and $t_d$ being the differential time between beam emission (as sensed by the transducer 130 at the probe 122) and reception by the sensor 120 at $t_0$. Signal injection into the probe 122 at $t_0+nT+t_d$ has the effect of creating an artificial echo that seems to come from the sensor 120 position, n frames after the detection frame. The steps are repeated to actualize the position of the sensor 120. Frame rate estimation may also be repeated periodically to account for possible parameter changes as the user changes the imaging settings (imaging mode, settings, and depth may all affect frame rate). The timeline of FIG. 5 depicts the sequence of events for this embodiment. Note that the external system's clock is totally independent from the scanner's clock.

Figure 6:
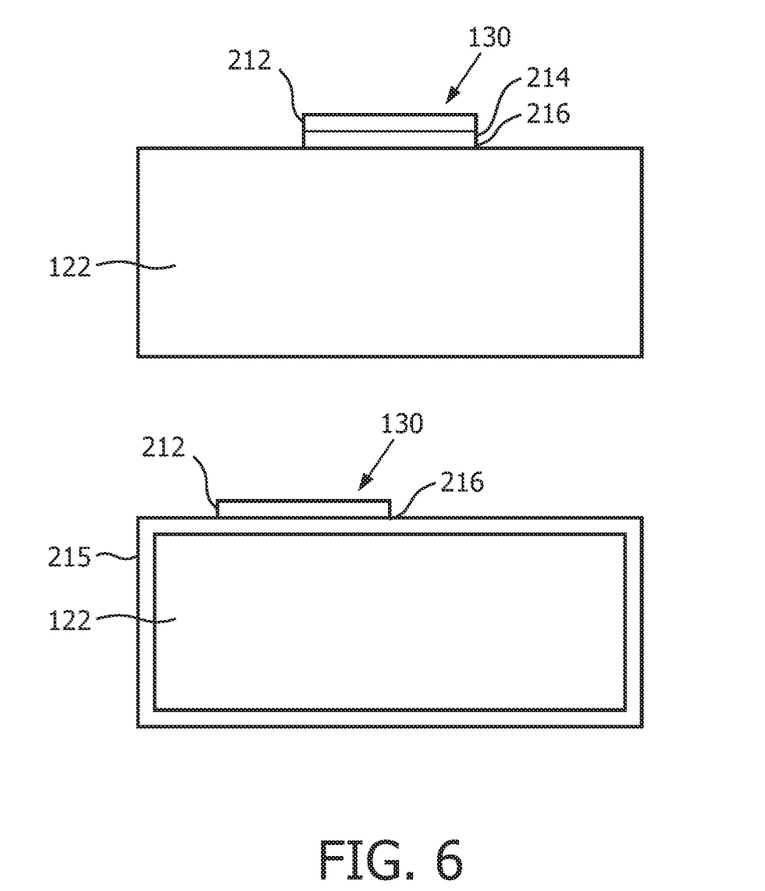
FIG. 6 is a plan view of two embodiments showing a transducer mounting on a probe in accordance with the present principles.

Referring to FIG. 6, a number of embodiments for the transducer 130 at the probe 122 or sensor 120 on the instrument 102 may be employed. A transducer(s) 130 at the probe 112 should not interfere with the scanner's imaging operation. The transducers 130 may be made by a thin piece of PVDF foil or strip 212 (e.g., 5 MHz PVDF foil) spanning part of an aperture (around the edges) or small PZT transducers close to the central elements of the probe 122. These transducers 130 are preferably integrated as part of a special sterile cover used to wrap the probe 122 for sterile procedures. The PVDF strip 212 could be integrated into a disposable sheath structure 215 and may be used for sterilization in many cases. An acoustic matching layer 214 could be integrated into the strip 212. A form of glue or coupling medium 216 could be integrated into the strip 212 for binding to the probe (or sheath 215) without air bubbles. The glue 216 could be temporary or permanent. The strip 212 could completely cover the probe surface, or cover it partially, or be placed in different regions, as exemplified in FIG. 6, which shows different configurations for strip 212 on the probe 122.

Figure 7A:
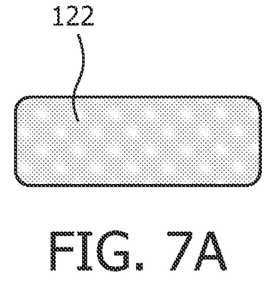
FIGS. 7A-7I show a plurality of configurations for mounting a transducer on a probe in accordance with the present principles.
Figure 7B:
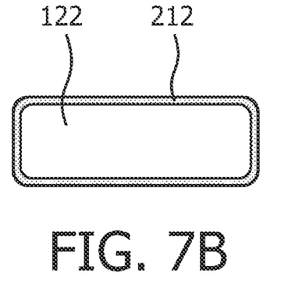
Figure 7C:
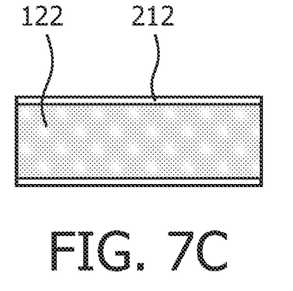
Figure 7D:
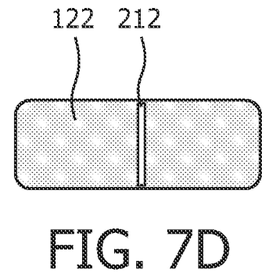
Figure 7E:
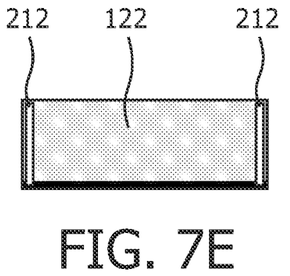
Figure 7F:
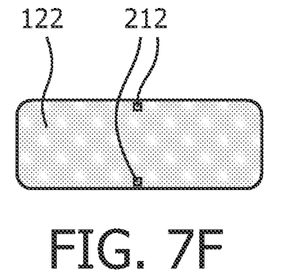
Figure 7G:
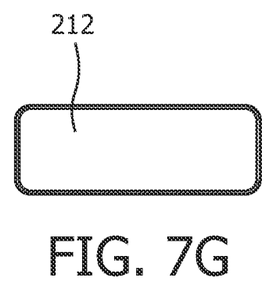
Figure 7H:
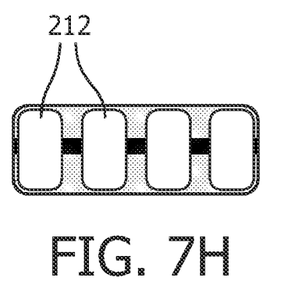
Figure 7I:
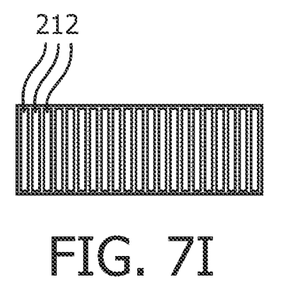

Referring to FIGS. 7A-7I, possible embodiments for line trigger detectors/signal injectors placed at the surface of the probe 122 include the following. A front view of probe 122 is shown in FIG. 7A. FIG. 7B shows a foil 212 running along the edges of the probe 122. FIG. 7C shows a PVDF foil 212 running along only elevational edges of the probe. FIG. 7D shows a PVDF foil 212 across a central element of the probe 122. FIG. 7E shows a PVDF foil 212 along first and last elements of the probe 122. FIG. 7F shows a PVDF or small PZT foil 212 at a top and bottom of a central element of the probe 122. FIG. 7G shows a PVDF foil 212 covering the entire surface of the probe 122. FIG. 7H shows n≥2 PVDF strips 212 at the surface of the probe 122 (to break left-right symmetry). FIG. 7I shows a plurality of PVDF strips 212 across the probe surface to compensate for beamforming effects.

The strip or strips 212 may be employed for detecting the firing of individual beams, or for injecting a signal, or both. The PVDF strip 212 could consist of multiple sub-strips, providing a better granularity of the acoustic fields from the probe 122. This could be useful for identifying a 'first' beam in sector probes or larger probes, thereby estimating the frame rate and "start frame" signals. Multiple sub-strips could be fired with time delays and apodization to optimize the marker response on the image.

Figure 8:
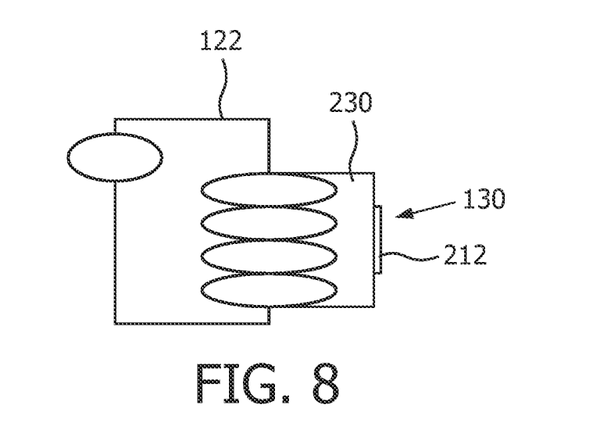
FIG. 8 depicts a glove on a user grasping a probe, the glove having a transducer mounted thereon in accordance with the present principles.

Referring to FIG. 8, in another embodiment, the strip 212 is mounted on a disposable glove 230. The glove 230 is employed by a user to hold the probe 122, and thus the glove 230 having the strip 212 provides the same functionality as described above for the strip 212.

Figure 9:
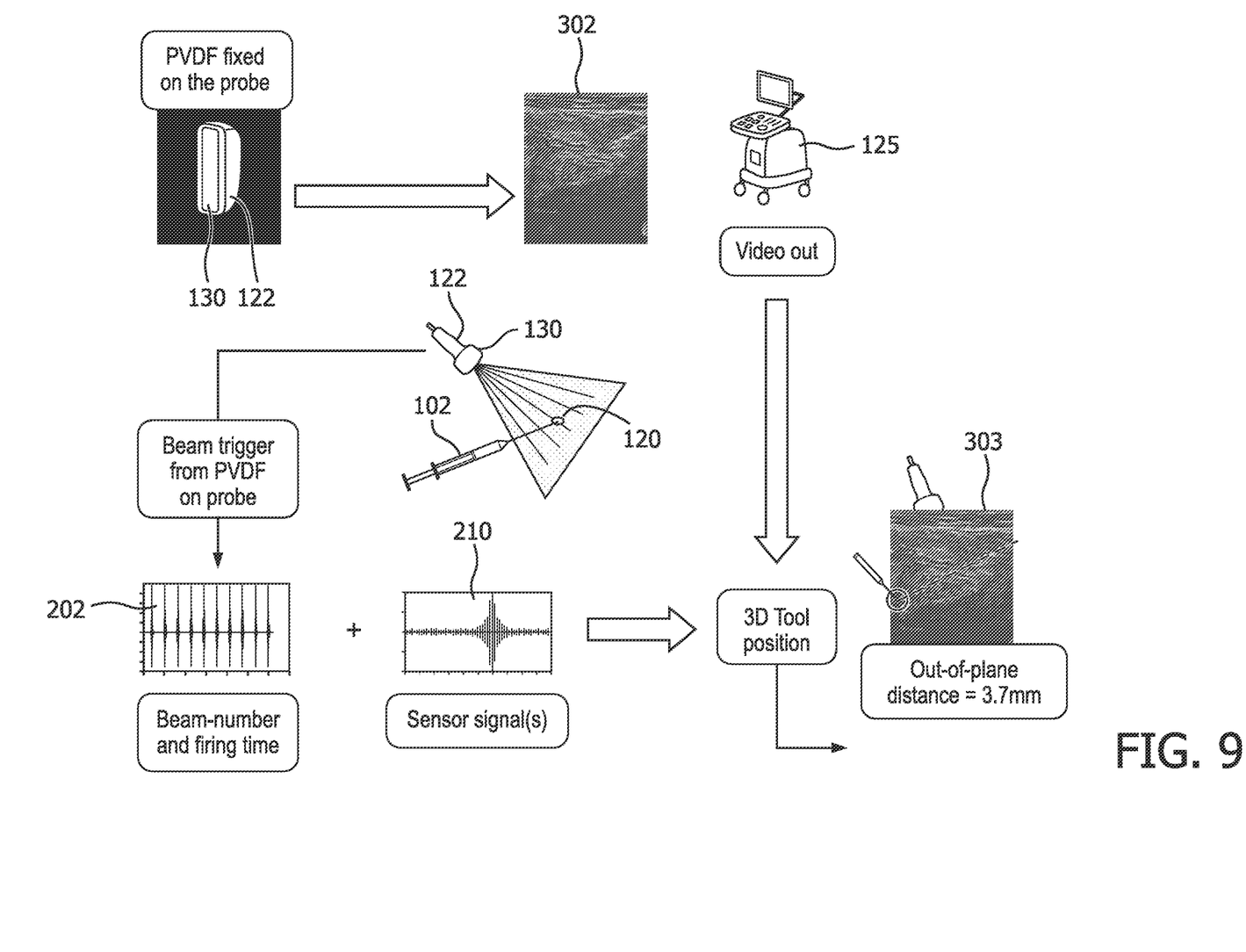
FIG. 9 is a conceptual diagram showing a system for tracking an instrument with ultrasound in accordance with another embodiment.

Referring to FIG. 9 with continued reference to FIG. 1, a conceptual diagram shows interaction between components in accordance with another illustrative embodiment. The ultrasound sensor 120 is placed on the instrument 102, e.g., at the tip of a needle. That sensor 120 senses ultrasound signals as beams from an imaging probe (122) sweep of the field of view, together with the transducer 130 (PVDF) strip that detects each beam as it is fired. The video-out signal is available from the scanner 125 and is streamed into the computational workstation 112.

An appropriate image 302 is cropped and segmented to identify the parts of the image that correspond to the left and right beams fired by the scanner 125. Image processing is performed by the image processing module 115 (FIG. 1). At any given moment, the transducer 130 (e.g., PVDF strip) on the US probe 122 provides a signal (A) when any of the US beams have been fired. This signal goes to the control module 124. Additionally, the instrument 102 (with a PVDF sensor(s)) also receives this acoustic wave and converts it into an electrical signal (B), which also goes to the control module 124. The control module 124 is connected to or part of the computational workstation 112.

When the system starts, only the A-signals are measured, and used to identify the inter-beam time and the inter-frame time. A one-time calibration step is run to estimate the frame rate (T) of the imaging mode being used. Using some asymmetry built into the strip 130, the beam corresponding to the start of the frame is differentiated from the one corresponding to the end of the frame. Each one is identified and the number of beams counted. After this step, the number of beams (NB), inter-beam times, and frame-rate are known.

Additionally, since most US scanners also provide a video-out, the video-out signal can be analyzed, together with the US signals, to quantitatively estimate the beam positions in the image. The real-time video-out image of the US probe 122 is used to crop the US image. For most scanners/images, equally dividing the image 150 into NB scan-lines 152 will suffice, as shown in FIG. 10.

When a tool or instrument 102 is inserted into a patient or field of view, the instrument 102 receives a signal based on its location inside the image. The primary beam that includes the sensor 120 can be automatically detected based on the maximum interpolated signals. Since after the calibration, the beam timings are known, the range/depth of the sensor 120 can also be computed from the time difference between the emission of the beam (signal-A peak) and the acoustic wave reaching the sensor 120 (signal-B peak). Note that this information is available since signal-A and signal-B are time-synced since they are connected to the same control module 124. Additionally, since the beam position in a video image 303 has already been established, the instrument 102 position can now be displayed on top of the US image in real-time.

In one embodiment, a first step is to estimate the frame rate T of the imaging probe 122. One way this can be done is by listening to the received signal for a relatively long time $T_{est}$ (e.g., a quarter of a second, allowing to record 10 frames at 40 Hz) and analyzing it for its dominant period, i.e., by Fourier analysis. The received trace 202 may look like what is depicted in FIG. 3. On that trace 202, the individual impulses correspond to different beams hitting the sensor 120 (the amplitude varies as beams get closer and then farther from the sensor 120). The pattern is then repeated several times as several identical frames are acquired in continuous sequence. To make the algorithm simple and robust, multiple strips (on the sensor 120) could be deployed to differentiate the beginning of the frame from the end of the frame. Alternately, an asymmetric strip could be used to create this differentiation.

Once the calibration is complete, the video image is divided up into the individual beams as depicted in FIG. 10. This would establish the location of the individual beam inside the US image. Once this is done, the receive system (e.g., workstation 112) analyzes traces from the sensor 120 on the instrument 102. Note that after the calibration, acquisition of these traces is now synchronized with the frame rate. The workstation 112 searches for the temporal maximum to of this trace (trace 210). That maximum corresponds to the instant when the pulse from the transmit event that is best aligned with the sensor 120 reaches the sensor 120 (See FIG. 4 where the trace received by the sensor is used to find the time to when the most on-axis transmit reaches the sensor. $t_0$ in this case is simply the temporal maximum of the trace 210).

At this point, the workstation 112 can compute the depth of the sensor 120 by using the time when the acoustic pulse was transmitted at the probe (signal-A peak) and when the US-pulse was received at the instrument 102 (signal-B peak), multiplied by the average speed of sound in tissue (e.g., 1540 m/s). Additionally, since the first beam of the frame is known from the continuous signal-A trace, the workstation 112 can also compute the beam-number on which the sensor 120 lies. Together, the above steps provide the accurate position of the sensor 120 and/or needle-tip in the US image. This can be overlaid on top of a US image 302 for accurate visualization as shown in image 303.

Note that the beam-forming parameters may be improved by iterating through multiple frames, or to re-do the calibration every few frames. Since the present principles do not change anything in the US scanner's imaging pipeline, and can do all the analysis in real-time, the calibration can even be done in every individual frame.

In some embodiments, the beam-parameters can be recalibrated every time a change is detected in the video-out image. Additionally, the instrument or needle 102 may have more than one sensor implanted therein, the signal from which could be used to estimate its out-of-plane position. Furthermore, to make the method easier to implement, the transducer 130 may include a PVDF or PZT strip and may be made of two or more strips, e.g., one on the left and the other on the right. This would break the symmetry in the beam-firing patterns and help differentiate the start of the image-frame (first beam on one strip) from the end (last beam on the other strip). Alternately, the strip could be cut in a non-symmetric manner to generate a non-symmetric profile as the fired beams move left to right.

The workstation 112 could also try to corroborate the response of the needle tip 102 on the video-out US image 303 with the position that has been tracked by the system itself. In most cases, these would have a strong correlation, showing the correctness of the system. If this correlation starts to drift, then the system would automatically trigger a self-check on its calibration parameters. Instead of simple peak detection for identifying the beam closest to the sensor and the arrival time, it may be advantageous to fit the curves of FIG. 3 (signals received by the sensor during $T_{est}$) and fit the curve of the local maxima of the individual pulses to a simple signal model, e.g., a Gaussian. It may also be desirable for the injected signal to blink while the position of the needle 102 is shown on the image 303. If the videostream is captured and synchronized to the signal acquisition and injection setup, differential images can be generated to highlight the injected signal (the "blink off" image is subtracted from the "blink on" image). The differential images can be enhanced and superimposed on the original image in an entirely image-processing chain that only needs to access video data from the scanner 125. Variations could also include different visualizations (shapes, etc.), or multiple mounting embodiments.

Figure 11:
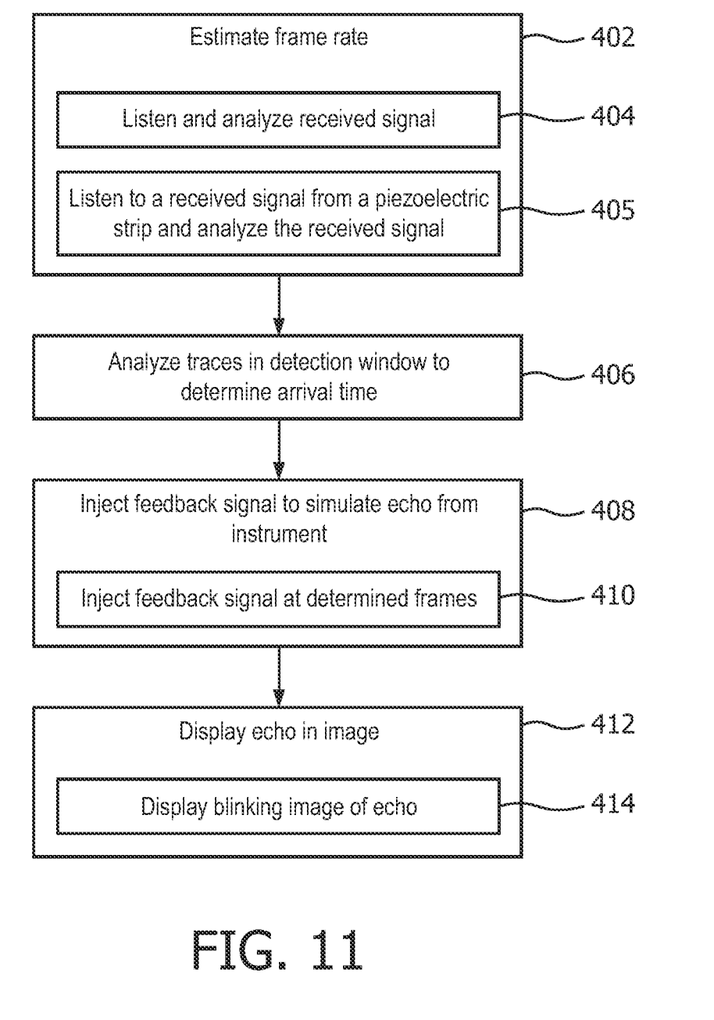
FIG. 11 is a flow diagram showing a method for tracking an instrument with ultrasound in accordance with one illustrative embodiment.

Referring to FIG. 11, a method for determining a position of an instrument is shown in accordance with one embodiment. In block 402, a frame rate of an imaging probe is estimated. In block 404, estimating the frame rate may include listening to a received signal for a period of time, and analyzing the received signal to determine its dominant period. In block 405, an asymmetric piezoelectric strip may be placed on the imaging probe. Estimating the frame rate may include listening to a received signal from the asymmetric piezoelectric strip on the probe and analyzing the received signal to determine its dominant period. That way, even the start of frame lines can be identified.

In block 406, traces are analyzed to determine if they are within a detection window to find a temporal maximum which best matches a position of a sensor mounted on an instrument to determine an arrival time. The detection window includes a detection time $T_{detect}$, which may be between T and 2T, where T is the frame rate; however, if T is known, listening for a time T is sufficient if synchronized with the start-of-frame signals. If not, optionally, listen for a little bit longer (e.g., 1.2T) to make sure that beam interpolation is possible.

In block 408, an acoustic feedback signal is injected into the imaging probe using a transducer on the imaging probe to simulate an echo back from the sensor mounted on the instrument. In block 410, the acoustic feedback signal is injected in frames at $t_0+nT+t_d$, where $t_0$ is a temporal maximum of signals received by the sensor, $t_d$ is a delay inserted to simulate an echo back from the sensor, T is frame rate and n is an integer.

In block 412, the echo is displayed in an image to identify the position of the instrument. In block 414, displaying the echo in an image may include causing the echo to blink in the image. Other image effects may also be employed (shapes, etc.).

Figure 12:
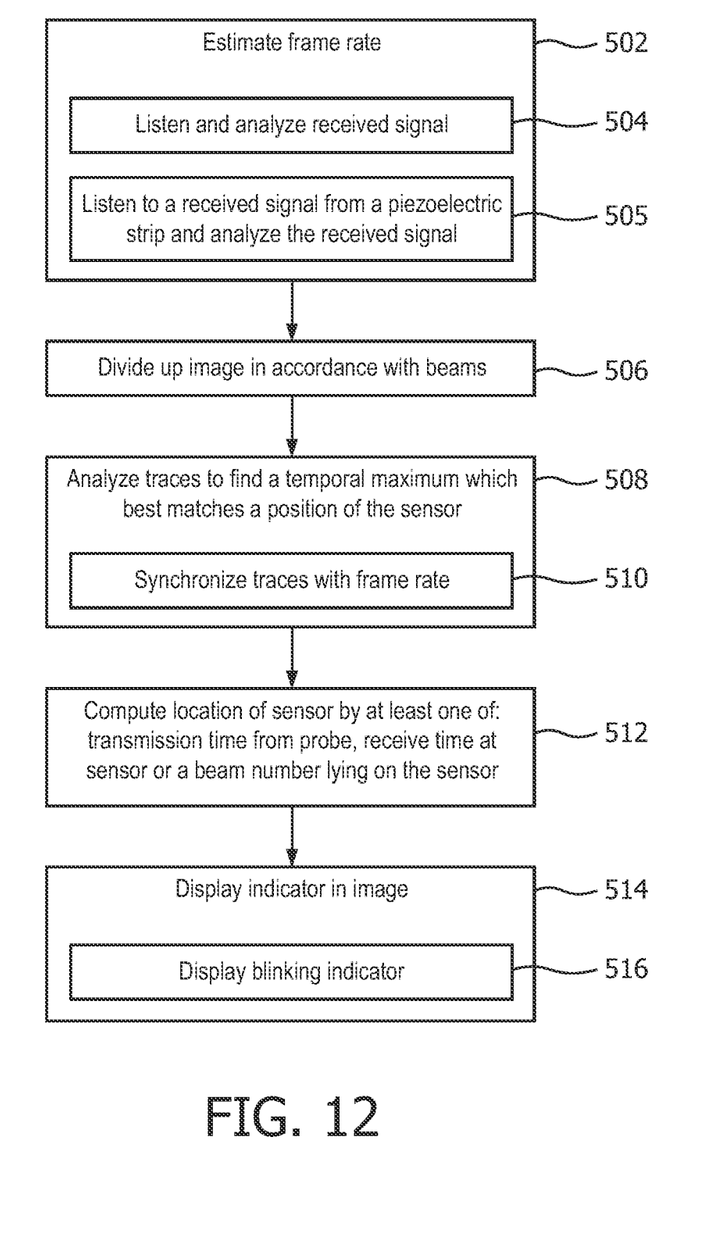
FIG. 12 is a flow diagram showing a method for tracking an instrument with ultrasound in accordance with another illustrative embodiment.

Referring to FIG. 12, a method for determining a position of an instrument is shown in accordance with another embodiment. In block 502, a frame rate of an imaging probe is estimated. In block 504, estimating the frame rate may include listening to a received signal for a period of time, and analyzing the received signal to determine its dominant period. In block 505, an asymmetric piezoelectric strip may be placed on the imaging probe. Estimating the frame rate may include listening to a received signal from the asymmetric piezoelectric strip on the probe and analyzing the received signal to determine its dominant period. That way, even the start of frame lines can be identified.

In block 506, an image is divided up into individual beams to establish a location of an individual beam in the image. In block 508, traces are analyzed to find a temporal maximum which best matches a position of a sensor mounted on an instrument to determine an arrival time. This may include synchronizing the traces with the frame rate in block 510. In block 512, computing at least one of: a location of the sensor using a transmission time from the probe and a receive time at the sensor, and a beam number on which the location of the sensor lies to determine the position of the sensor. In block 514, an indicator is overlaid on the image to visually indicate the location of the instrument. In block 516, displaying the indicator includes displaying a blinking indicator in the image. Other image effects may also be employed (shapes, etc.).

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for scanner independent tracking of interventional instruments (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for tracking with ultrasound an instrument inserted in a body, the instrument including an acoustic sensor, the system comprising:

an acoustic transducer on an ultrasound probe, wherein the ultrasonic probe is configured to emit ultrasound imaging signals into the body, the acoustic transducer configured to (i) sense the ultrasound imaging signals as the ultrasound imaging signals are being emitted from the ultrasonic probe and (ii) generate a first control signal indicating a time when a particular ultrasound imaging signal of the sensed ultrasound imaging signals is fired from the ultrasonic probe, wherein the acoustic transducer is coupled to the ultrasonic probe via a coupling medium situated between the acoustic transducer and the ultrasonic probe; and a control module operatively connected to the ultrasonic probe with the acoustic transducer, the control module configured to:

receive, from the acoustic transducer, the first control signal indicating the time when the particular ultrasound imaging signal is fired from the ultrasonic probe, receive, from the acoustic sensor, a second control signal indicating a time when the particular ultrasound imaging signal arrived at the acoustic sensor, and determine a three-dimensional location of the instrument based at least in part on the received first control signal from the acoustic transducer and the received second control signal from the acoustic sensor.

2. The system as recited in claim 1, wherein the control module is configured to cause the acoustic transducer to inject an acoustic signal to the ultrasonic probe to highlight a position of the acoustic sensor in an image of the instrument, wherein the injected acoustic signal simulates an echo back from the acoustic sensor.

3. The system as recited in claim 2, wherein the acoustic signal injected to the ultrasonic probe is injected in frames at $t_0+nT+t_d$, where $t_0$ is a temporal maximum of the ultrasound imaging signals received by the acoustic sensor, $t_d$ is a delay, corresponding to an ultrasound time of flight from the ultrasonic probe to the acoustic sensor, inserted to simulate an echo back from the acoustic sensor to the ultrasonic probe, and T is a frame rate and n is an integer.

4. The system as recited in claim 2, further comprising a display configured to display images collected using the ultrasonic probe, the images including a bright area based on the acoustic signal injected to the ultrasonic probe.

5. The system as recited in claim 1, wherein the acoustic transducer is mounted directly to the ultrasonic probe via the coupling medium.

6. The system as recited in claim 1, wherein the acoustic transducer is mounted on a sheath covering the ultrasonic probe via the coupling medium.

7. The system as recited in claim 1, wherein the acoustic transducer includes one or more piezoelectric strips.

8. The system as recited in claim 2, wherein the control module is further configured to estimate beam positions in the image, and to determine a position of the instrument based on the beam positions by computing frame rate and number of beams in an ultrasonic signal transmitted from the ultrasonic probe.

9. The system as recited in claim 1, wherein the coupling medium is a form of glue, and the acoustic transducer is coupled to the ultrasonic probe by the glue binding the acoustic transducer directly to the ultrasonic probe or to a sheath covering the ultrasonic probe.

\* \* \* \* \*